(12) United States Patent
Boley et al.

(10) Patent No.: US 11,202,159 B2
(45) Date of Patent: Dec. 14, 2021

(54) METHODS OF SELF-CALIBRATING OF A HEARING DEVICE AND RELATED HEARING DEVICES

(71) Applicant: GN Hearing A/S, Ballerup (DK)

(72) Inventors: Jonathan Boley, Mundelein, IL (US); Tobias Piechowiak, Ballerup (DK)

(73) Assignee: GN Hearing A/S, Ballerup (DK)

( * ) Notice: Subject to any disclaimer, the term of this patent is extended or adjusted under 35 U.S.C. 154(b) by 0 days.

(21) Appl. No.: 15/703,708

(22) Filed: Sep. 13, 2017

(65) Prior Publication Data

US 2019/0082278 A1 Mar. 14, 2019

(51) Int. Cl.
*H04R 25/00* (2006.01)
*A61B 5/12* (2006.01)

(52) U.S. Cl.
CPC ............ *H04R 25/70* (2013.01); *H04R 25/30* (2013.01); *H04R 25/305* (2013.01); *H04R 25/50* (2013.01); *A61B 5/121* (2013.01)

(58) Field of Classification Search
CPC ........ H04R 25/70; H04R 25/30; H04R 25/50; A61B 5/121
See application file for complete search history.

(56) References Cited

U.S. PATENT DOCUMENTS

| | | | |
|---|---|---|---|
| 6,792,114 B1 | 9/2004 | Kates et al. | |
| 8,045,737 B2 * | 10/2011 | Stirnemann | H04R 25/70 381/312 |
| 9,374,638 B2 * | 6/2016 | Petersen | H04R 25/30 |
| 2007/0036377 A1 * | 2/2007 | Stirnemann | H04R 25/505 381/315 |
| 2010/0246869 A1 * | 9/2010 | Zhang | H04R 25/70 381/320 |
| 2013/0170660 A1 * | 7/2013 | Kristensen | H04R 25/30 381/60 |
| 2014/0321657 A1 * | 10/2014 | Stirnemann | A61B 5/125 381/60 |
| 2015/0172839 A1 | 6/2015 | Rung | |

FOREIGN PATENT DOCUMENTS

| | | |
|---|---|---|
| EP | 1594344 A2 | 11/2005 |
| EP | 1594344 A3 | 3/2006 |
| EP | 2 234 414 A2 | 9/2010 |
| EP | 2 234 414 A3 | 1/2012 |

(Continued)

OTHER PUBLICATIONS

Extended European Search Report dated Jan. 15, 2019 for corresponding U.S. patent Application No. 18191597.6.

(Continued)

*Primary Examiner* — Sunita Joshi
(74) *Attorney, Agent, or Firm* — Vista IP Law Group, LLP

(57) ABSTRACT

A method for self-calibrating of a hearing device (which includes an ear canal microphone, an external microphone, and a receiver) includes: obtaining an input signal with the external microphone; providing an output signal with the receiver; measuring the output signal using the ear canal microphone; predicting an output response based on a gain setting; determining a difference between the predicted output response and the measured output signal; and calibrating the hearing device by controlling a gain parameter based on the difference.

33 Claims, 3 Drawing Sheets

(56) References Cited

FOREIGN PATENT DOCUMENTS

EP          2 744 227 A1    6/2014
WO   WO 2013/075255 A1    5/2013

OTHER PUBLICATIONS

Non-Final Office Action dated Jun. 24, 2020 for related U.S. Appl. No. 16/033,605.
"Communication Pursuant to Article 94 (3) dated Jan. 27, 2020 for correspondingEuropean Application No. 17 190 783.5".
"Scheperele, Rachel A et al "Further Assessment of Forward Pressure Level for inSitu Calibration" The journal of the acoustical society of America, vol. 130, No. 6,Dec. 2011, pp. 3882-3892".
"Extended European Search Report dated Feb. 20, 2018 for correspondingEuropean Application No. 17190783.5, 7 Pages."

* cited by examiner

METHODS OF SELF-CALIBRATING OF A HEARING DEVICE AND RELATED HEARING DEVICES

FIELD

The present disclosure relates to methods of self-calibrating of a hearing device and related hearing devices.

BACKGROUND

We usually calibrate hearing instruments based on some average ear canal response. However, an individual ear may be very different than an average ear. The recommended practice for calibrating hearing aids is usually to verify the gain with real-ear measurements and adjust as needed. Real ear calibration is performed using a probe tube in the ear canal.

However, this calibration practice is a costly and time-consuming procedure, and therefore often skipped.

SUMMARY

Accordingly, there is a need for hearing devices capable of and methods for self-calibrating of a hearing device, which can be used in absence of real ear measurement systems.

A method for self-calibrating of a hearing device is disclosed. The hearing device comprises an ear canal microphone, an external microphone and a receiver. The method comprises: obtaining an input signal with the external microphone; transmitting an output signal with the receiver; measuring the output signal using the ear canal microphone. The method may comprise predicting an output response based on gain settings and determining a difference between the predicted output response and the measured output signal. The method comprises calibrating the hearing device by controlling a gain parameter based on the difference.

Further, a hearing device is provided, the hearing device comprising: a set of microphones comprising an external microphone for provision of an input signal, and an ear canal microphone for measuring an output signal; a processor for processing input signals and providing a processed output signal based on input signals; and a receiver for transmission of an output signal. The hearing device may comprise a controller configured to control hearing device settings. The hearing device is configured to predict an output response based on gain settings; determine a difference between the predicted output response and the measured output signal; and calibrate the hearing device by controlling the gain parameter based on the difference.

It is an advantage of the present disclosure that it enables a hearing device to calibrate itself to a given ear which would be beneficial to both users and dispensers. The present disclosure may achieve gains closer to target without use of probe tube measurements.

A method for self-calibrating of a hearing device (which includes an ear canal microphone, an external microphone, and a receiver) includes: obtaining an input signal with the external microphone; providing an output signal with the receiver; measuring the output signal using the ear canal microphone; predicting an output response based on a gain setting; determining a difference between the predicted output response and the measured output signal; and calibrating the hearing device by controlling a gain parameter based on the difference.

Optionally, the act of obtaining the input signal comprises determining one or more characteristics of the input signal.

Optionally, the act of obtaining the input signal comprises determining one or more characteristics of the input signal in one or more frequency bands.

Optionally, the act of measuring the output signal comprises determining a forward pressure level of the output signal.

Optionally, the act of controlling the gain parameter comprises adjusting a band gain in one or more frequency bands.

Optionally, the act of controlling the gain parameter comprises determining a gain by reducing or minimizing the difference between the predicted output response and the measured output signal.

Optionally, the act of determining the difference between the predicted output response and the measured output signal is performed based on one or more hearing device configuration parameters.

Optionally, the act of determining the difference between the predicted output response and the measured output signal is performed based on an initial hearing device calibration setting.

Optionally, the act of determining the difference between the predicted output response and the measured output signal is performed based on one or more algorithm parameters.

Optionally, the act of determining the difference between the predicted output response and the measured output signal comprises estimating an ear geometry.

Optionally, the act of estimating the ear geometry comprises determining one or more ear canal parameters.

Optionally, the act of estimating the ear geometry comprises categorizing an ear.

Optionally, the one or more ear canal parameters comprises an ear canal length, an ear canal width, a conicity of an ear canal, an ear volume, an insertion depth, or any combination of the foregoing.

Optionally, the act of determining the one or more ear canal parameters is performed based on an estimate of real-ear unaided gain, an user input, an acoustic measurement, or any combination of the foregoing.

Optionally, the act of predicting the output response is performed based on the initial hearing device calibration setting.

Optionally, the receiver is in an ear canal part of the hearing device.

Optionally, the act of obtaining the input signal comprises obtaining a measurement signal from an external device.

A hearing device includes: a receiver for providing an output signal; a set of microphones comprising an external microphone for provision of an input signal, and an ear canal microphone for measuring the output signal; and a processor for providing a processed output signal based on the input signal; wherein the hearing device is configured to predict an output response based on a gain setting, determine a difference between the predicted output response and the measured output signal, and calibrate the hearing device by controlling a gain parameter based on the difference.

DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
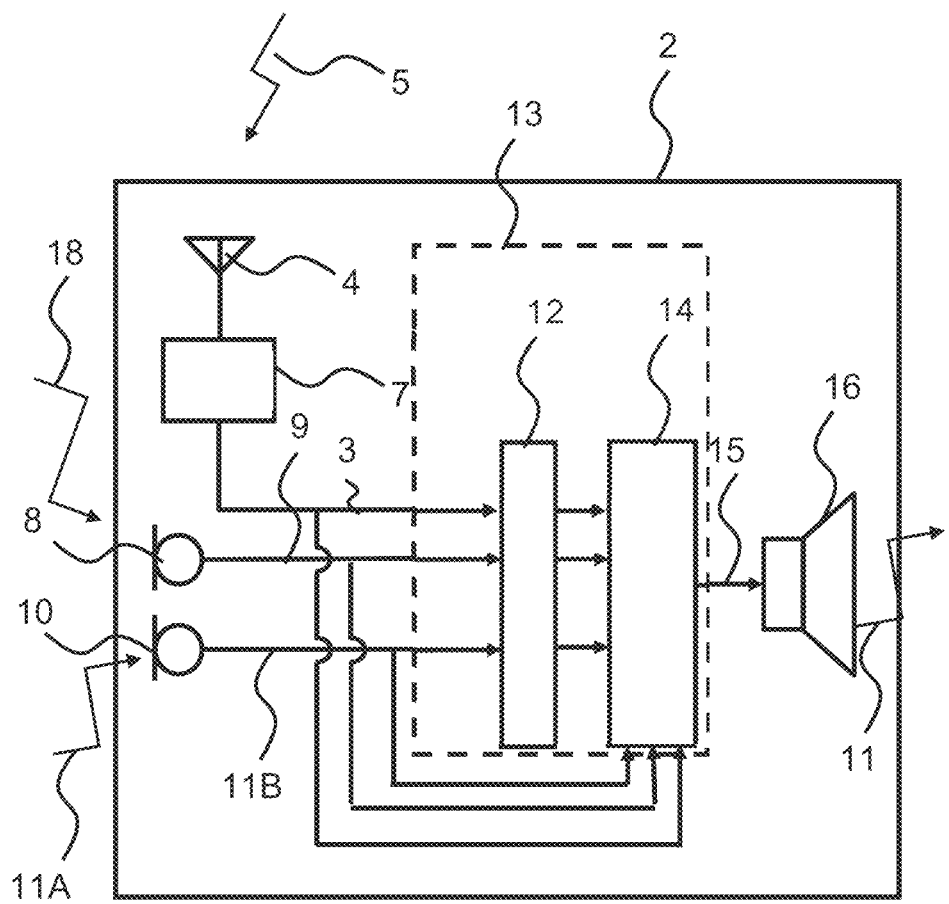
FIG. 1 schematically illustrates an exemplary hearing device according to this disclosure, FIG. 2 schematically illustrates a cross-section of an exemplary hearing device partly inserted in an ear canal of a user.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The inventors have found that pinna is responsible for most of the variations in insertion-gain (& directional cues) across individuals, and an ear canal microphone (placed in the ear canal) actually captures most of these variations. Residual variance is due to the length resonance of the ear canal which is direction-independent and varies less across individuals. The present disclosure permits to find a good approximation of these individual resonances (i.e., looking at the feedback path), and thereby obtain a much better and more customized estimation of the insertion gain. It is an advantage of the present disclosure that a flat insertion gain is obtained for the disclosed hearing devices without further measurements (i.e. without any real-ear measurements).

A method for self-calibrating of a hearing device is disclosed. The hearing device comprises an ear canal microphone, an external microphone and a receiver. The method is performed at the hearing device. The method relates to self-calibration by the hearing device. The method comprises obtaining an input signal with the external microphone.

In one or more exemplary methods, obtaining an input signal with the external microphone comprises measuring the input signal using the external microphone. For example, obtaining an input signal with the external microphone comprises measuring the input signal using the external microphone and analysing the input signal.

The method comprises transmitting an output signal with the receiver and measuring the output signal using the ear canal microphone. In one or more exemplary methods, the hearing device may comprise one or more ear canal microphones and measuring the output signal may be performed using the one or more ear canal microphones. The output signal may be a specific measurement signal and/or an environmental signal. The measured output signal may be denoted as an ear canal microphone input signal indicative of the output signal as the measured output signal relates the output signal as measured and taken as input in the ear canal microphone. The measured output signal may be seen as the output signal affected by the ear canal properties. The present disclosure allows quantifying the transformation of the output signal transmitted based on the measure output signal (or ear canal microphone input signal indicative thereof), which in turn results in estimation of the ear geometry, leading to a self-calibration of the hearing device.

The method may comprise predicting an output response based on gain settings and determining a difference between the predicted output response and the measured output signal. In one or more exemplary methods, predicting the output response may be performed based on gain settings of the hearing device and/or device calibration of the hearing device (such as factory or default device calibration). Such a device calibration is performed during design/manufacturing, based on an ear simulator and/or average ear. Device calibration may include a coupler response for flat-insertion gain (CORFIG), which is a correction that is applied to the output of a hearing-aid in order to provide a flat gain when the hearing device is inserted. A standard CORFIG may be based on an average ear and thus may represent a standard measure that does not account for individual differences in ear canal geometry.

In one or more exemplary methods, determining a difference between the predicted output response and the measured output signal comprises determining a difference between the predicted output magnitude spectrum and the measured output magnitude spectrum. Predicting the output response may be performed using the output signal at the receiver. It is an advantage of this disclosure that the output response may be predicted despite the fact that the reference for measuring insertion gain, i.e. Real Ear Unaided Response (REUR), is unknown. Predicting the output response may be influenced by near-field effects when the ear canal or external microphone and receiver are in very close proximity to each other. It is seen as an advantage of the present disclosure that near-field effects are accounted for because the present disclosure allows the physical ear geometry to be estimated.

In one or more exemplary methods, determining a difference between the predicted output response and the measured output signal comprises comparing the input signal received at the external microphone and the measured output signal received (i.e. forming an ear canal microphone input signal) at the ear canal microphone. If the receiver and the ear canal microphone responses are known, the natural resonance of the open ear canal or the effect of occluding the ear can be accounted for. Alternatively, or additionally, the ear canal microphone response can be assumed as flat and the receiver response can be assumed as approximating the open ear response. With the disclosed method, the measured transducer response (receiver to ear canal microphone) approximates the real ear unaided response (REUR).

In one or more exemplary methods, determining the difference may comprise predicting an insertion gain by comparing the signals at the external microphone and at the ear canal microphone, and subtracting the measured transducer response (receiver to ear canal microphone).

The method comprises calibrating the hearing device by controlling a gain parameter based on the difference. The gain parameter may be an insertion gain, which is the difference between the sound pressure level measured near the ear drum with a hearing device in place, and the sound pressure level measured in the unaided ear.

In one or more exemplary methods, obtaining the input signal comprises determining one or more characteristics of the input signal. For example, a characteristic may comprise a distortion and/or a spectrum, such as an amplitude (e.g. maximum amplitude) and/or a phase.

In one or more exemplary methods, obtaining the input signal comprises determining one or more characteristics of the input signal in one or more frequency bands. For example, the one or more characteristics of the input signal are measured or determined for each frequency band separately.

In one or more exemplary methods, measuring the output signal comprises determining a forward pressure level of the measured output signal. Sound pressure measured by an ear canal microphone can be decomposed into forward pressure level and reflected pressure level.

In one or more exemplary methods, controlling the gain parameter comprises adjusting a band gain in one or more frequency bands.

In one or more exemplary methods, controlling the gain parameter comprises determining the gain by minimizing the difference between the predicted output response and the measured output signal.

In one or more exemplary methods, determining the difference between the predicted output response and the measured output is based on one or more hearing device configuration parameters. For example, one or more hearing device configuration parameters may comprise a receiver placement, a receiver response, an external microphone placement, an external microphone response, an ear canal microphone placement, an ear canal microphone response, a presence of venting (opening or not), placement of opening if any, a dome and/or vent size, a dome and/or vent placement, and/or an expected device insertion depth.

In one or more exemplary methods, determining the difference between the predicted output response and the measured output is based on an initial hearing device calibration setting.

In one or more exemplary methods, determining the difference between the predicted output response and the measured output is based on one or more algorithm parameters. For example, the one or more algorithm parameters may be indicative of characteristics of the algorithm, such as interaction of spectral bands, non-linearity.

In one or more exemplary methods, determining the difference between the predicted output response and the measured output signal comprises estimating an ear geometry. The ear geometry may refer to an ear shape, ear canal dimensions, and/or properties the ear or ear canal in space. In one or more exemplary methods, the ear geometry may comprise ear dimensions, and/or ear canal type. Determining the difference between the predicted output response and the measured output signal may be seen as calculating an error between the predicted output response and the measured output signal. In one or more exemplary methods, determining the difference between the predicted output response and the measured output signal may comprise estimating other parameters of the ear canal, such as one or more tympanic membrane properties. Determining the difference between the predicted output response and the measured output signal may take into account hearing device configurations.

In one or more exemplary methods, estimating the ear geometry comprises determining one or more ear canal parameters. In one or more exemplary methods, the one or more ear canal parameters comprise one or more of an ear canal length, an ear canal width, a conicity of the ear canal, an ear volume and/or an insertion depth of the ear canal microphone and/or of the receiver.

In one or more exemplary methods, estimating the ear geometry comprises categorizing an ear, such as categorizing an ear canal. For example, one or more categories may be predetermined. A plurality of categories may lead to more accuracy in estimating the ear geometry. Categorizing an ear or an ear canal may be performed based on the ear canal parameter. Categorizing an ear or an ear canal may comprise identifying an ear canal type indicative of the present ear or ear canal under test. It may also be seen that categorizing an ear or an ear canal comprises estimating the ear geometry.

In one or more exemplary methods, determining the ear canal parameter is based on an estimate of real-ear unaided gain, user input and/or acoustic measurement. For example, determining the ear canal parameter may be based on an analysis of the measured output signal and the predicted output signal. For example, the input and output signals (measured by the two microphones) may be compared to estimate ear canal parameters. In determining the difference between the predicted output response and the measured output signal, the inventors have determined that a length resonance often results in a spectral notch in the output response at the ear canal microphone, and the frequency of this notch varies with the residual ear canal length. The ear canal length can thereby be determined. Once the frequency of the notch of the output response at the ear canal microphone is identified, a canal length that is expected to result in a notch at this frequency is determined using the category. An appropriate real-ear insertion gain (REIG) correction for this ear canal may be determined based on an expected spectral difference between the locations of the ear canal microphone and the tympanic membrane. To correct the insertion gain, the method may comprise applying the inverse of the predicted real-ear insertion gain (assuming target gain is 0 dB). It may be envisaged that as predictions are not perfect, a fraction of the predicted real-ear insertion gain may be used as a conservative correction.

In one or more exemplary methods, predicting the output response is based on the initial hearing device calibration setting.

In one or more exemplary methods, the receiver is placed in an ear canal part of the hearing device. In one or more exemplary methods, the hearing device comprises an ear canal microphone and an ear canal receiver, where the ear canal microphone and the receiver are placed in the ear canal part of the hearing device. These exemplary methods may provide a real-ear insertion gain (REIG) that is flat for the user. In one or more exemplary method, determining a difference between the predicted output response and the measured output signal may comprise measuring the difference in transfer function from the receiver to the open-ear (REUR) and from the receiver to the external microphone (L-MiE, Lateral Microphone). The relationship between REIG, the receiver response itself (RecToEar), L-MiE and the open-ear transfer function (REUR) may be expressed in the following way:

$$REIG = REAR - REUR$$
$$= L\text{-}MiE + RecToEar - REUR$$
$$= L\text{-}MiE - REUR + RecToEar$$
$$= RecToEar - (REUR - L\text{-}MiE)$$

where REAR denotes real-ear aided response, i.e. the response when the hearing device is inserted in the ear canal of the user.

It can be seen that making the receiver response similar to the REUR-MiE response results in a flat insertion gain. The present disclosure allows a flat insertion gain to be obtained across a large number of customers and direction of arrival by just inserting the device into the ear canal. No extra equipment is needed.

In one or more exemplary methods, obtaining the input signal comprises obtaining a specific measurement signal from an external device. The input signal may be denoted an external microphone input signal.

The disclosed may be performed when explicitly requested (e.g. by putting the hearing device in a calibration mode), and/or each time the device is turned on, and/or continuously.

A hearing device is disclosed. The hearing device may be a hearing aid, wherein the processor is configured to compensate for a hearing loss of a user.

The hearing device may be of the behind-the-ear (BTE) type, in-the-ear (ITE) type, in-the-canal (ITC) type, receiver-in-canal (RIC) type or receiver-in-the-ear (RITE) type. The hearing device may be a binaural hearing aid. The hearing device may comprise a first earpiece and a second earpiece, wherein the first earpiece and/or the second earpiece is an earpiece as disclosed herein.

The hearing device may comprise an antenna for converting one or more wireless input signals, e.g. a first wireless input signal and/or a second wireless input signal, to an antenna output signal. The wireless input signal(s) origin from external source(s), such as spouse microphone device(s), wireless TV audio transmitter, and/or a distributed microphone array associated with a wireless transmitter.

The hearing device may comprise a transceiver, which may comprise a radio transceiver coupled to the antenna for converting the antenna output signal to a transceiver input signal. Wireless signals from different external sources may be multiplexed in the radio transceiver to a transceiver input signal or provided as separate transceiver input signals on separate transceiver output terminals of the radio transceiver. The hearing device may comprise a plurality of antennas and/or an antenna may be configured to be operate in one or a plurality of antenna modes. The transceiver input signal comprises a first transceiver input signal representative of the first wireless signal from a first external source.

The hearing device comprises a set of microphones. The set of microphones may comprise one or more microphones. The set of microphones comprises an external microphone for provision of an input signal, and an ear canal microphone for measuring an output signal transmitted by a receiver and received at the ear canal microphone. In other words, the ear canal microphone is configured to measure the output signal as an ear canal microphone input signal.

The set of microphones may comprise one or more external microphones. The set of microphones may comprise one or more ear canal microphones. The set of microphones may comprise N microphones for provision of N microphone signals, wherein N is an integer in the range from 1 to 10. In one or more exemplary hearing devices, the number N of microphones is two, three, four, five or more. The set of microphones may comprise a third microphone for provision of a third microphone input signal.

In one or more exemplary hearing devices, the ear canal microphone may be positioned on the internal side of the hearing device (directed into the ear canal and facing the ear drum) and the external microphone may be positioned on the external side of the hearing device (capturing the environment). It is an advantage of the present disclosure to use these microphones, rather than a probe microphone, to measure the response inside the ear canal. As used in this specification, the term "external microphone" refers to any microphone that is for receiving, sensing, detecting, or capturing sound in an environment, such as external sound in an environment outside a user of the hearing device. Accordingly, the word "external" in the term "external microphone" does not indicate the position of the external microphone with respect to the hearing device. The external microphone may be located inside or outside the hearing device.

The hearing device comprises a processor for processing input signals and for providing a processed output signal based on input signals.

The hearing device comprises a receiver for transmission of an output signal and a controller configured to control hearing device settings. The hearing device is configured to predict an output response based on gain settings. The hearing device is configured to determine a difference between the predicted output response and the measured output signal; and calibrate the hearing device by controlling the gain parameter based on the difference.

In one or more exemplary hearing devices, the hearing device comprises a processing unit including the processor and the controller.

The present disclosure relates to a hearing device comprising an ear canal part (i.e. a part of the hearing device inserted in the ear canal of the ear) and an ear canal receiver and an ear canal microphone, which are placed in the ear canal part and are configured to achieve a flat insertion gain.

The present disclosure relates to a hearing-device receiver comprising a microphone-and-receiver-in-the-ear module, wherein the microphone-and-receiver in-the-ear module comprises an ear canal receiver and an ear canal microphone.

The figures are schematic and simplified for clarity, and they show details to assist the understanding of the embodiments. Throughout, the same reference numerals are used for identical or corresponding parts.

FIG. 1 is a block diagram of an exemplary hearing device according to the disclosure.

The hearing device 2 comprises a receiver 16 for transmission of an output signal 15. The receiver 16 may be configured to emit an audio output signal 11 based on the output signal 15.

A receiver 16 is configured to emit an audio output signal 11, e.g. to be directed towards an eardrum of the hearing device user.

The hearing device 2 may comprise an antenna 4 for converting a first wireless input signal 5 of a first external source (not shown in FIG. 1) to an antenna output signal. The hearing device 2 may comprise a transceiver 7 for provision of a transceiver input signal 3, which may comprise a radio transceiver coupled to the antenna 4 for converting the antenna output signal to one or more transceiver input signals.

The hearing device comprises a set of microphones comprising an external microphone 8 for obtaining an input signal 9 (i.e. an external microphone input signal). The external microphone 8 may be configured to provide based on the received audio input signal 18 an input signal 9 to other modules of the hearing device 2.

The set of microphones comprises an ear canal microphone 10 for receiving an audio output signal 11A from a receiver 16, and for taking the received audio output signal 11A as an input signal. The ear canal microphone 10 is configured to measure the output signal 11B based on the audio output signal 11A received from the receiver 16 because the ear canal microphone 10 provides an ear canal microphone input signal 11B based on the output signal 11B which is based on the audio output signal 11A transformed by the ear canal properties. The audio output signal 11A received as input at the ear canal microphone 10 is affected by the ear canal properties. The output signal 11B (i.e. ear canal microphone input signal 11B) measured in this disclosure relates to the audio output signal 11A as received in the ear canal microphone, the audio output signal 11 as emitted by the receiver 16, and the output signal 15 as provided to the receiver 16.

The hearing device 2 comprises a controller 12 configured to control hearing device settings.

The hearing device 2 comprises a processor 14 connected to the controller 12 for receiving and processing signals. The processor 14 is configured to compensate for a hearing loss of a user and to provide an electrical output signal 15 based on input signals.

The hearing device 2 or the processor 14 is configured to predict an output response based on gain settings. The hearing device 2 or the processor 14 is configured to determine a difference between the predicted output response and the measured output signal.

In one or more exemplary hearing devices, the hearing device 2A comprises a processing unit 13 including the processor 14 and the controller 12. The processing unit 13 is configured to control hearing device parameters, to compensate for hearing loss The hearing device 2 may comprise an ear canal part and another part towards the opening of the ear. In one or more exemplary hearing devices, the ear canal microphone 10 is positioned in the ear canal part of the hearing device 2, i.e. the part facing the ear drum or tympanic membrane) and the external microphone 8 is positioned on the part of the hearing device 2 that faces the opening of the ear (capturing the environment).

In one or more exemplary hearing devices, the processing unit 13 is configured to predict an output response based on gain settings of the hearing device and to determine a difference between the predicted output response and the measured output signal.

In one or more exemplary hearing devices, determining a difference between the predicted output response and the measured output signal comprises comparing the input signal received at the external microphone and the output signal measured at the ear canal microphone as ear canal microphone input signal. The hearing device 2 may be configured to determine the difference between the predicted output response and the measured output signal by estimating an ear parameter such as the ear canal length. As a length resonance results in a spectral notch in the output response at the ear canal microphone 8, and the frequency of this notch varies with the residual ear canal length, the hearing device 2 determines the ear canal length based on identification of the frequency of the notch and categorization of the frequency. Once the frequency of the notch of the output response at the ear canal microphone is identified, a canal length that is expected to result in a notch at this frequency is determined using the category. The hearing device 2 may determine an appropriate real-ear insertion gain (REIG) correction for the ear canal based on an expected spectral difference between the locations of the ear canal microphone and the tympanic membrane.

The hearing device 2 is configured to calibrate the hearing device by controlling the gain parameter based on the difference. To correct the insertion gain, the hearing device may apply the inverse of the predicted real-ear insertion gain, such as applying half of the predicted real-ear insertion gain.

Figure 2:
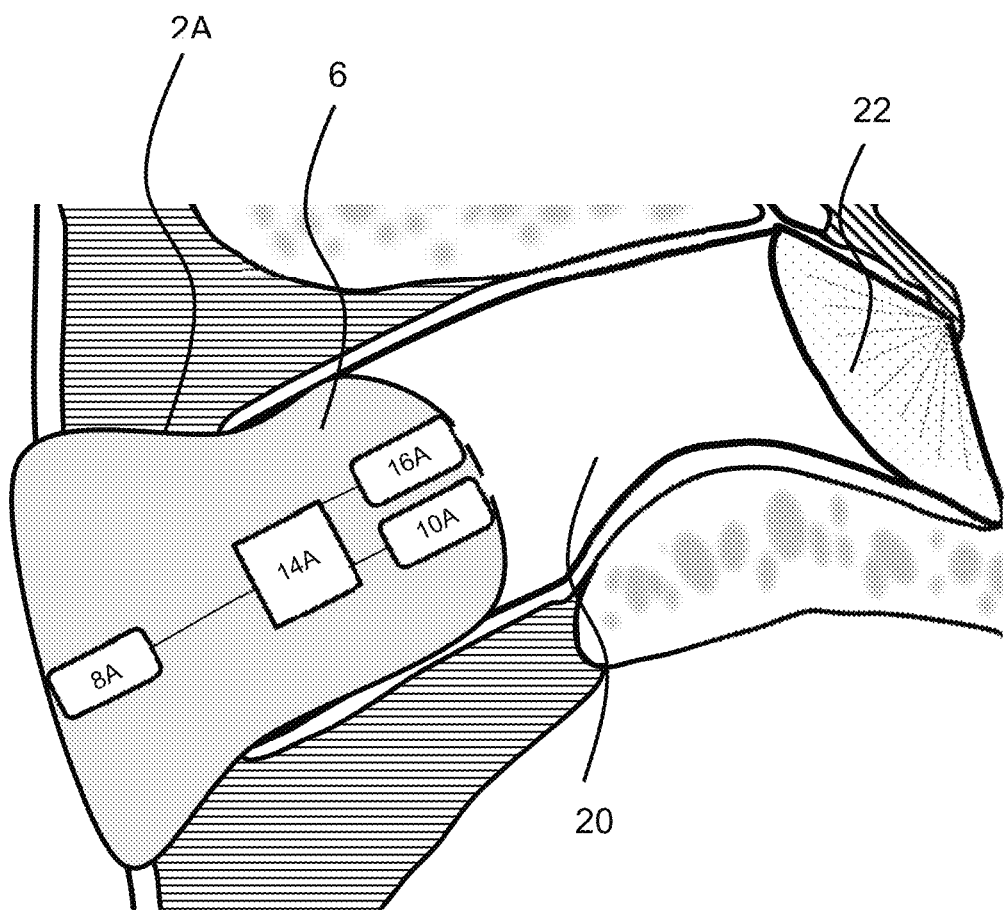

FIG. 2 is a cross-section of a user's ear having an exemplary hearing device 2A partly inserted in the ear canal 20 of the ear according to the disclosure. The hearing device 2A is an in-the-ear hearing device. The hearing device 2A comprises a housing 6, a receiver 16A, an external microphone 8A for obtaining an input signal and an ear canal microphone 10A. The receiver 16A is placed in an ear canal part of the hearing device 2A, and thereby called an ear canal receiver 16A. The hearing device 2A comprises the ear canal microphone 10A and the ear canal receiver 16A, which are placed facing the ear drum or tympanic membrane 22. The hearing device 2A comprises a processor 14A configured to compensate for a hearing loss of a user. The receiver 16A is configured to transmit an output signal to be directed towards an eardrum of the hearing device user. The ear canal microphone 10A is configured to measure the output signal emitted by the receiver 16A because the ear canal microphone 10A receives the output signal from the receiver 16A as an ear canal microphone input signal. The output signal received as input at the ear canal microphone 10A is affected by the ear canal properties. The processor 14A is configured to predict an output response based on gain settings. The processor 14A is configured to determine a difference between the predicted output response and the measured output signal. In one or more exemplary hearing devices, determining a difference between the predicted output response and the measured output signal comprises comparing the input signal received at the external microphone and the output signal received at the ear canal microphone (for forming an input signal to the ear canal microphone).

Figure 3:
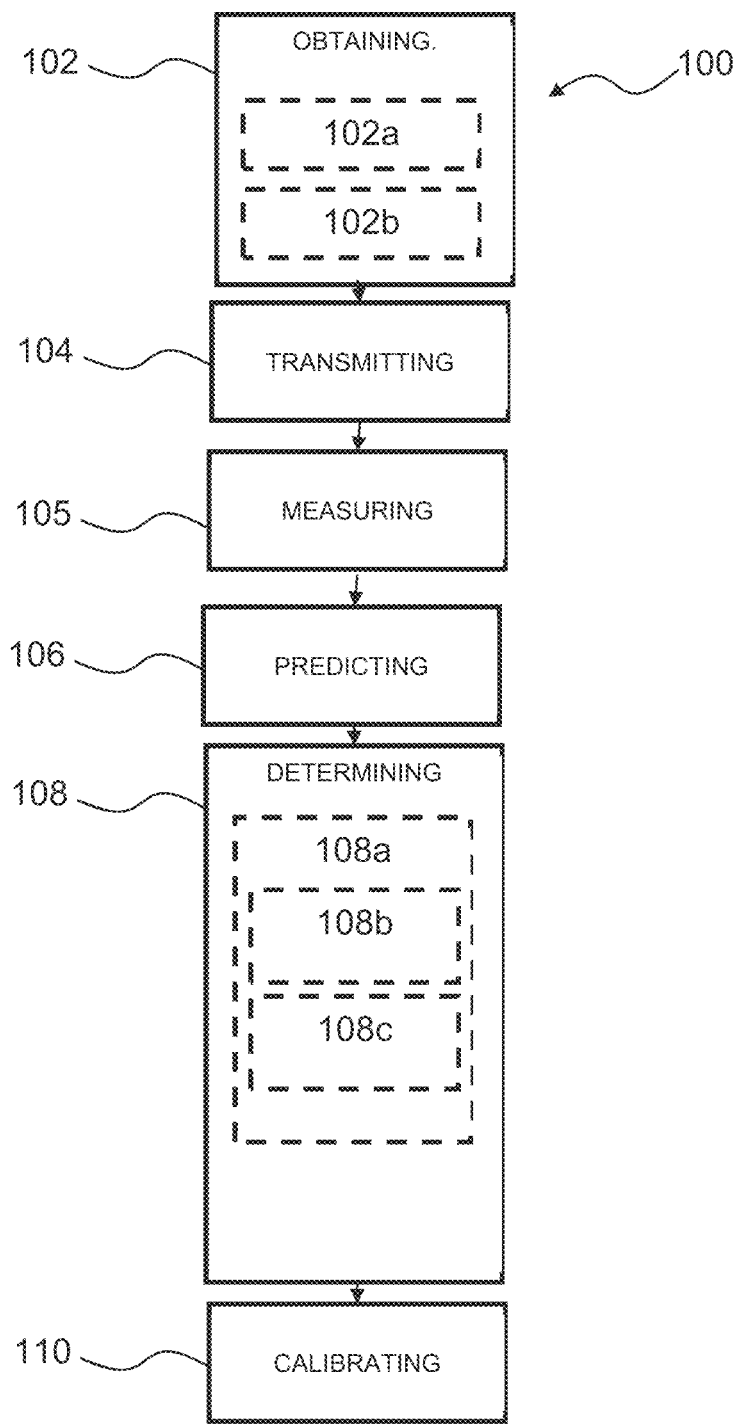
FIG. 3 is a flow diagram of an exemplary method according to the disclosure.

FIG. 3 shows a flow diagram of an exemplary method of self-calibrating of a hearing device according to some embodiments. The hearing device comprises an ear canal microphone, an external microphone and a receiver. The method comprises obtaining 102 an input signal with the external microphone.

In one or more methods, obtaining 102 an input signal with the external microphone comprises measuring 102a the input signal using the external microphone, e.g. using the external microphone and analysing the input signal.

The method 100 comprises transmitting 104 an output signal with the receiver and measuring 105 the output signal using the ear canal microphone. In one or more exemplary methods, output signal may be a specific measurement signal and/or an environmental signal.

The method 100 comprises predicting 106 an output response based on gain settings, and/or optionally device calibration (such as factory or default device calibration). The method 100 comprises determining 108 a difference between the predicted output response and the measured output signal.

In one or more exemplary methods, determining 108 a difference between the predicted output response and the measured output signal comprises determining a difference between the predicted output magnitude spectrum and the measured output magnitude spectrum. Predicting 106 the output response may be performed using the output signal as transmitted by the receiver.

In one or more exemplary methods, determining 108 a difference between the predicted output response and the measured output signal comprises comparing the input signal received at the external microphone and the output signal received as an ear canal microphone input signal at the ear canal microphone. If the receiver and the ear canal microphone responses are known, the natural resonance of the open ear canal or the effect of occluding the ear can be accounted for. Alternatively, or additionally, the ear canal microphone response can be assumed as flat and the receiver response can be assumed as approximating the open ear response. With the disclosed method, the measured transducer response (receiver to ear canal microphone) approximates the real ear unaided response (REUR).

In one or more exemplary methods, determining 108 the difference may comprise determining an insertion gain by comparing the signals at the external microphone and at the ear canal microphone, and subtracting the measured transducer response (receiver to ear canal microphone).

The method comprises calibrating 110 the hearing device by controlling a gain parameter based on the difference. For example, controlling the gain parameter comprises adjusting a band gain in one or more frequency bands. In one or more exemplary methods, controlling the gain parameter comprises determining the gain by minimizing the difference between the predicted output response and the measured output signal.

In one or more exemplary methods, obtaining 102 the input signal comprises determining 102b one or more characteristics of the input signal, such as in one or more frequency bands. For example, a characteristic may comprise a distortion and/or a spectrum, such as an amplitude (e.g. maximum amplitude) and/or a phase.

In one or more exemplary methods, measuring 105 the output signal comprises determining a forward pressure level of the measured output signal. Sound pressure measured by an ear canal microphone can be decomposed into forward pressure level and reflected pressure level. The present disclosure relates to determining the forward pressure level of the measure output signal.

In one or more exemplary methods, determining 108 the difference between the predicted output response and the measured output is based on one or more hearing device configuration parameters.

In one or more exemplary methods, determining 108 the difference between the predicted output response and the measured output is based on an initial hearing device calibration setting.

In one or more exemplary methods, determining 108 the difference between the predicted output response and the measured output is based on one or more algorithm parameters. For example, the one or more algorithm parameters may be indicative of characteristics of the algorithm, such as interaction of spectral bands, non-linearity.

In one or more exemplary methods, determining 108 the difference between the predicted output response and the measured output signal comprises estimating 108a an ear geometry. For example, determining 108 the difference between the predicted output response and the measured output signal may comprise estimating other parameters of the ear canal, such as one or more tympanic membrane properties. Determining the difference between the predicted output response and the measured output signal may take into account ear canal information (e.g. user-supplied information about ear canal geometry (e.g., large/small, male/female, head circumference, etc.)) and/or hearing device configurations. Predicting ear canal dimensions may be performed based on acoustic measurements according to this disclosure.

In one or more exemplary methods, estimating 108a the ear geometry comprises determining 108b an ear canal parameter. The ear canal parameter may comprise an ear canal size and/or an ear canal length.

In one or more exemplary methods, estimating 108a the ear geometry comprises categorizing 108c an ear. For example, one or more categories may be predetermined. A plurality of categories may lead to more accuracy in estimating the ear geometry. Categorizing an ear may be performed based on the ear canal parameter. It may also be seen that categorizing an ear comprises estimating the ear geometry.

In one or more exemplary methods, determining 108b the ear canal parameter is based on an estimate of real-ear unaided gain, user input and/or acoustic measurement. In determining the difference between the predicted output response and the measured output signal, the inventors have determined that a length resonance often results in a spectral notch in the output response at the ear canal microphone, and the frequency of this notch varies with the residual ear canal length. The ear canal length can thereby be determined. Once the frequency of the notch of the output response at the ear canal microphone is identified, a canal length that is expected to result in a notch at this frequency is determined using the category. An appropriate real-ear insertion gain (REIG) correction for this ear canal may be determined based on an expected spectral difference between the locations of the ear canal microphone and the tympanic membrane. To correct the insertion gain, the method may comprise applying the inverse of the predicted real-ear insertion gain (assuming target gain is 0 dB). Because predictions may not be perfect, a fraction of the predicted real-ear insertion gain may be used as a conservative correction. If the target gain is not a flat (e.g. 0 dB at all frequencies), the target gain may be subtracted from the predicted gain before using it as a correction factor.

In one or more exemplary methods, predicting 106 the output response is based on the initial hearing device calibration setting.

In one or more exemplary methods, obtaining 102 the input signal comprises obtaining a specific measurement signal from an external device.

The use of the terms "first", "second", "third" and "fourth", etc. does not imply any order, but are included to identify individual elements. Moreover, the use of the terms first, second, etc. does not denote any order or importance, but rather the terms first, second, etc. are used to distinguish one element from another. Note that the words first and second are used here and elsewhere for labelling purposes only and are not intended to denote any specific spatial or temporal ordering. Furthermore, the labelling of a first element does not imply the presence of a second element and vice versa.

One or more of the features described may be incorporated or implemented in accordance with any of the items described below:

Item 1. A method for self-calibrating of a hearing device, the hearing device comprising an ear canal microphone, an external microphone and a receiver, the method comprising: obtaining an input signal with the external microphone; providing an output signal with the receiver; measuring the output signal using the ear canal microphone; predicting an output response based on gain setting(s); determining a difference between the predicted output response and the measured output signal; and calibrating the hearing device by controlling a gain parameter based on the difference.

Item 2. The method according to item 1, wherein the act of obtaining the input signal comprises determining one or more characteristics of the input signal.

Item 3. The method according to any of the preceding items, wherein the act of obtaining the input signal comprises determining one or more characteristics of the input signal in one or more frequency bands.

Item 4. The method according to any of the preceding items, wherein the act of measuring the output signal comprises determining a forward pressure level of the output signal.

Item 5. The method according to any of the preceding items, wherein the act of controlling the gain parameter comprises adjusting a band gain in one or more frequency bands.

Item 6. The method according to any of the preceding items, wherein the act of controlling the gain parameter comprises determining a gain by reducing or minimizing the difference between the predicted output response and the measured output signal.

Item 7. The method according to any of the preceding items, wherein the act of determining the difference between the predicted output response and the measured output signal is performed based on one or more hearing device configuration parameters.

Item 8. The method according to any of the preceding items, wherein the act of determining the difference between the predicted output response and the measured output signal is performed based on an initial hearing device calibration setting.

Item 9. The method according to any of the preceding items, wherein the act of determining the difference between the predicted output response and the measured output signal is performed based on one or more algorithm parameters.

Item 10. The method according to any of the preceding items, wherein the act of determining the difference between the predicted output response and the measured output signal comprises estimating an ear geometry.

Item 11. The method according to item 10, wherein the act of estimating the ear geometry comprises determining one or more ear canal parameters.

Item 12. The method according to any of items 10-11, wherein the act of estimating the ear geometry comprises categorizing an ear.

Item 13. The method according to any of items 10-12, wherein the one or more ear canal parameters comprises an ear canal length, an ear canal width, a conicity of an ear canal, an ear volume, an insertion depth, or any combination of the foregoing.

Item 14. The method according to any of items 10-13, wherein the act of determining the ear canal parameter is based on an estimate of real-ear unaided gain, a user input, an acoustic measurement, or any combination of the foregoing.

Item 15. The method according to any of the preceding items as dependent on item 8, wherein the act of predicting the output response is based on the initial hearing device calibration setting.

Item 16. The method according to any of the preceding items, wherein the receiver is in an ear canal part of the hearing device.

Item 17. The method according to any of the preceding items, wherein the act of obtaining the input signal comprises obtaining a measurement signal from an external device.

Item 18. A hearing device comprising: a receiver for providing an output signal; a set of microphones comprising an external microphone for provision of an input signal, and an ear canal microphone for measuring the output signal; and a processor for providing a processed output signal based on the input signal; wherein the hearing device is configured to: predict an output response based on gain setting(s); determine a difference between the predicted output response and the measured output signal; and calibrate the hearing device by controlling a gain parameter based on the difference.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 2 hearing device
2A hearing device seen from a cross-section
3 transceiver input signal
4 antenna
5 first wireless input signal
6 housing
7 transceiver
8 external microphone
8A external microphone
9 input signal from external microphone
10 ear canal microphone
10A ear canal microphone
11 audio output signal emitted by the receiver
11A audio output signal received at the ear canal microphone
11B output signal provided as input to the processor by the ear canal microphone, i.e. the measured output signal or the ear canal microphone input signal
12 controller
13 processing unit
14 processor
14A processor
15 output signal from processor to the receiver
16 receiver
16A ear canal receiver
18 audio input signal at the external microphone
20 ear canal
22 ear drum or tympanic membrane
100 method of self-calibrating a hearing device
102 obtaining an input signal with the external microphone
102a measuring the input signal using the external microphone
102b determining one or more characteristics of the input signal
104 transmitting an output signal with the receiver and measuring 105 the output signal using the ear canal microphone
105 measuring the output signal using the ear canal microphone
106 predicting an output response based on gain settings
108 determining a difference between the predicted output response and the measured output signal
108a estimating an ear geometry
108b determining an ear canal parameter
108c categorizing an ear
110 calibrating the hearing device by controlling a gain parameter based on the difference

The invention claimed is:

1. A method performed by a hearing device, the hearing device comprising a first microphone, a processing unit, a receiver, and a second microphone, the second microphone being an ear canal microphone, the method comprising:
generating a microphone signal by the first microphone;
providing a processed output signal by the processing unit based on the microphone signal; and
providing an output sound by the receiver based on the processed output signal;
wherein a receiver response associated with the receiver corresponds with a difference between a real ear unaided response (REUR) and a microphone response (MiE) associated with the ear canal microphone.

2. The method of claim 1, wherein the receiver response imitates the difference between the real ear unaided response (REUR) and the microphone response (MiE) associated with the ear canal microphone.

3. The method of claim 1, further comprising providing a flat insertion gain by the hearing device.

4. The method of claim 3, wherein the flat insertion gain is provided without requiring any real ear measurement.

5. A hearing device comprising:
a first microphone configured to provide a microphone signal;
a processing unit configured to provide a processed output signal based on the microphone signal;
a receiver configured to provide output sound based on the processed output signal; and
a second microphone, the second microphone being an ear canal microphone;
wherein a receiver response associated with the receiver corresponds with a difference between a real ear unaided response (REUR) and a microphone response (MiE) associated with the ear canal microphone.

6. The hearing device of claim 5, wherein the receiver response is configured to imitate the difference between the real ear unaided response (REUR) and the microphone response (MiE) associated with the ear canal microphone.

7. The hearing device of claim 5, wherein the hearing device is configured to provide a flat insertion gain.

8. The hearing device of claim 7, wherein the hearing device is configured to provide the flat insertion gain without requiring any real ear measurement.

9. The hearing device of claim 5, further comprising a third microphone, the third microphone being an additional ear canal microphone.

10. The hearing device of claim 5, wherein the processing unit is configured to obtain an ear canal microphone signal from the ear canal microphone, and decompose the ear canal microphone signal into a forward pressure component and a reflected pressure component.

11. The hearing device of claim 5, wherein the processing unit is configured to
predict an output response;
determine a difference between the predicted output response and a measured output signal measured using the ear canal microphone; and
control a gain parameter based on the difference.

12. The hearing device of claim 11, wherein the processing unit is configured to control the gain parameter by reducing or minimizing the difference between the predicted output response and the measured output signal to determine a gain.

13. The hearing device of claim 11, wherein the processing unit is configured to determine the difference between the predicted output response and the measured output signal based on one or more hearing device configuration parameters.

14. The hearing device of claim 11, wherein the processing unit is configured to determine the difference between the predicted output response and the measured output signal based on an initial hearing device calibration setting.

15. The hearing device of claim 11, wherein the processing unit is configured to determine the difference between the predicted output response and the measured output signal based on one or more algorithm parameters.

16. The method of claim 1, wherein the receiver response is calibrated so that the receiver response corresponds with the difference between the real ear unaided response (REUR) and the microphone response (MiE) associated with the ear canal microphone.

17. The hearing device of claim 5, wherein the receiver response is calibrated so that the receiver response corresponds with the difference between the real ear unaided response (REUR) and the microphone response (MiE) associated with the ear canal microphone.

18. The method of claim 1, further comprising:
predicting an output response;
determining a difference between the predicted output response and a measured output signal measured using the ear canal microphone; and
controlling a gain parameter based on the difference.

19. The method of claim 1, further comprising determining one or more characteristics of the microphone signal.

20. The method of claim 19, wherein the one or more characteristics of the microphone signal is determined in one or more frequency bands.

21. The method of claim 1, further comprising obtaining ear canal microphone signal from the ear canal microphone, and decomposing the ear canal microphone signal into a forward pressure component and a reflected pressure component.

22. The method of claim 18, wherein the act of controlling the gain parameter comprises adjusting a band gain in one or more frequency bands.

23. The method of claim 18, wherein the act of controlling the gain parameter comprises determining a gain by reducing or minimizing the difference between the predicted output response and the measured output signal.

24. The method of claim 18, wherein the act of determining the difference between the predicted output response and the measured output signal is performed based on one or more hearing device configuration parameters.

25. The method of claim 18, wherein the act of determining the difference between the predicted output response and the measured output signal is performed based on an initial hearing device calibration setting.

26. The method of claim 18, wherein the act of determining the difference between the predicted output response and the measured output signal is performed based on one or more algorithm parameters.

27. The method of claim 1, further comprising estimating an ear geometry.

28. The method of claim 27, wherein the act of estimating the ear geometry comprises determining one or more ear canal parameters.

29. The method of claim 27, wherein the act of estimating the ear geometry comprises categorizing an ear.

30. The method of claim 28, wherein the one or more ear canal parameters comprises an ear canal length, an ear canal width, a conicity of the ear canal, an ear volume, an insertion depth, or any combination of the foregoing.

31. The method of claim 28, wherein the act of determining the one or more ear canal parameters is performed based on an estimate of real-ear unaided gain, an user input, an acoustic measurement, or any combination of the foregoing.

32. The method of claim 18, wherein the act of predicting the output response is performed based on an initial hearing device calibration setting.

33. The hearing device of claim 2, further comprising an ear canal microphone opening dedicated for only the ear canal microphone of the hearing device.

\* \* \* \* \*